United States Patent [19]

Calderon-Garciduenas

[11] Patent Number: 5,466,214
[45] Date of Patent: Nov. 14, 1995

[54] DYNAMIC HARNESS FOR HUMAN SPINE

[76] Inventor: Jose Calderon-Garciduenas, Paris #17 Col. Mirador, Monterrey, NL., Mexico, 64070

[21] Appl. No.: 253,285

[22] Filed: Jun. 2, 1994

[51] Int. Cl.[6] ........................................ A61F 5/00
[52] U.S. Cl. ........................ 602/19; 2/44; 128/DIG. 19
[58] Field of Search .................... 602/5, 19; 128/871, 128/873–876, DIG. 19; 2/44

[56] References Cited

U.S. PATENT DOCUMENTS

| 664,250 | 12/1900 | Fitzpatrick | 602/19 |
| 945,359 | 1/1910 | Adams | 602/19 |
| 1,650,650 | 11/1927 | Pieper | 602/19 |
| 1,930,378 | 10/1933 | Beagan | 128/875 X |
| 3,282,264 | 11/1966 | Connelly | 602/19 |
| 3,543,748 | 12/1970 | Charters | 602/19 |
| 4,541,419 | 9/1985 | Osawa | 602/19 |
| 5,259,833 | 11/1993 | Barnett | 602/19 |

*Primary Examiner*—Linda C. M. Dvorak
*Attorney, Agent, or Firm*—Laurence R. Brown

[57] ABSTRACT

This invention provides an improved dynamic harness for the human spine. The harness has adjustable supports for two shoulders, a belt and an elastic or semi-elastic band. The shoulder supports are coupled by a harnessing array with an upper suspender, a lower suspender and a crossed suspender.

3 Claims, 8 Drawing Sheets

DYNAMIC HARNESS FOR HUMAN SPINE

BACKGROUND OF THE INVENTION

For many years, in the medical practice of rehabilitation different types of harnesses have been used. These harnesses have the inconvenience of being rigid, extremely uncomfortable and difficult for the patient to wear for long time periods.

The present invention for the first time makes it possible in an orthopedic harness to move with relative comfort, because of the flexibility and elasticity. This has a significant advantage, because the comfortable use of this harness makes the patient willing to use it until he is completely recovered.

In addition, this harness has the advantage that it can be used not only as a corrective orthopedic harness, but also as a security harness in any kind of work that requires so much effort that the spine is in risk.

The present invention is applicable in a general way, to protect and avoid harm to the spine. Spine damage affects eight of each ten U.S. citizens in some period of their lives. For this reason government and private enterprise spend up to 36 billion dollars a year.

DESCRIPTION OF THE INVENTION

According to the pictures, the harness is built of scapulothoracic rings (1), with a lower strap section (2) allowing the person who is going to wear it to introduce his arms inside of them until the rings are completely mounted over the shoulders. The rings (1) are joined together by means of the upper (3) and lower (3') straps to which they stay bound at their ends. Also the strap are fastened at the center by the crossed suspender (4).

An important part of the harness is a band (5) which by suitable means, preferably seams, joins at its upper end to the lower strap (3') and at its lower end to the belt (6), thereby integrating in a single piece, the scapulothoracic rings (1), the straps (3, 3'), the band (5), and the belt (6).

Figure 6:
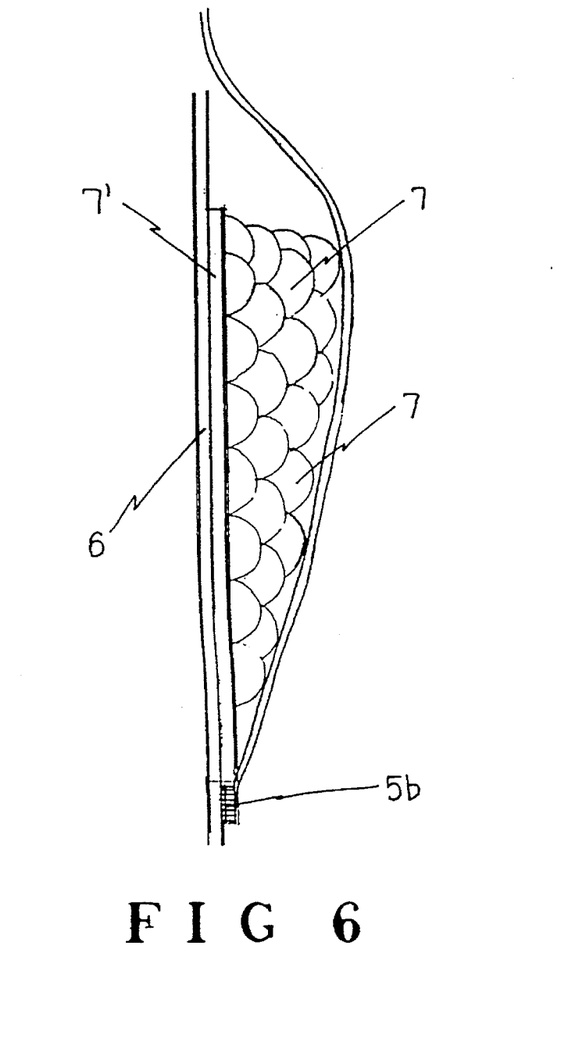
FIG. 6 shows a profile side view of the cushion section.
Figure 7:
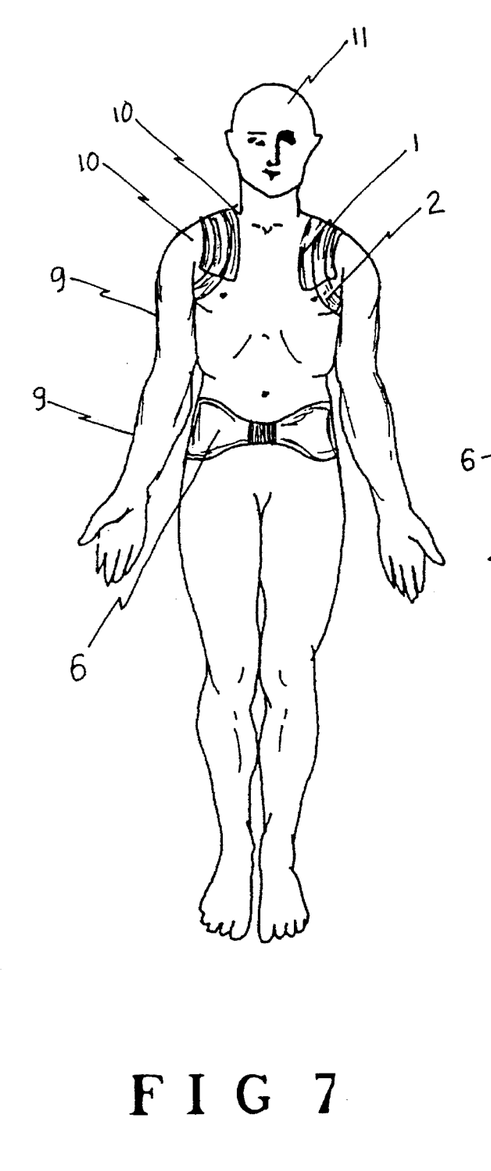
FIG. 7 shows a front view of a man wearing the harness.
Figure 7A:
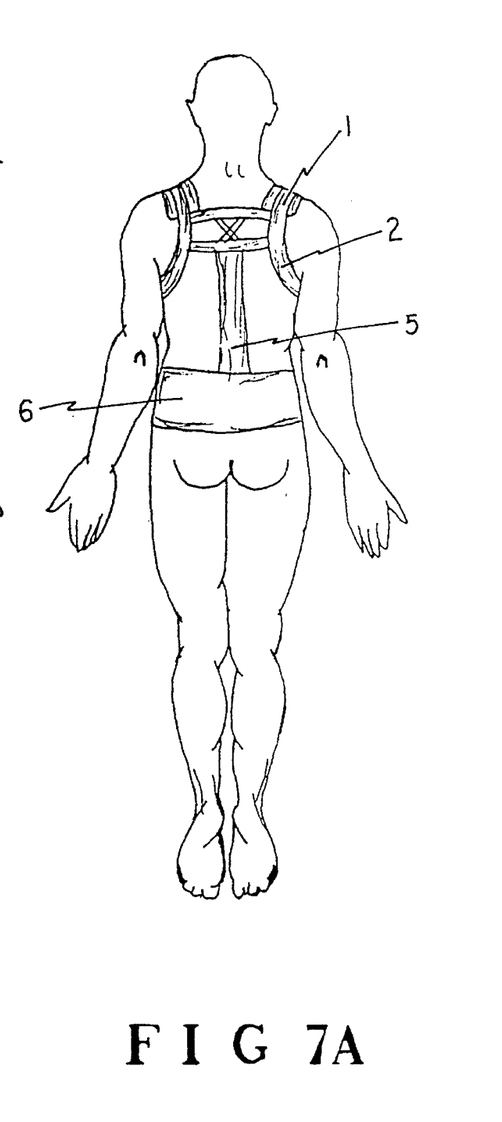
FIG. 7A shows a rear view of a man wearing the harness.

The belt (6) shapes the lower part of the harness and gives support to the lumbar region of the person wearing it. Also the belt (6) provides stability to the band (5) parallel to the spine of the person. The belt (6) has a cushion section (7) in the lumbosacral region, with a semiflexible core (7') to provide a greater support capacity. The cushion section (7) follows the normal contour of the spine, therefore is thicker in the upper part and thinner in the lower part (FIG. 6). The belt has at its ends appropriate means to fasten it to the waist of the person who wears the harness.

OPERATION METHOD

The dynamic spine harness works in a single piece having support points at the scapulothoracic rings and the belt. The human body has great mobility and one of its mobile parts is the spine with the function, besides movement, of carrying the weight of the body and the weight of any object carried. To carry objects manually, requires conditions of posture, strength and adequate limits of load to avoid injuries to the spine structures. The dynamic spine harness will give the user an additional support while carrying objects, as well as a feedback of his trunk posture, by increasing pressure in the support points of the harness. Therefore, the harness will provide a mechanical support and a feedback of the way the user is moving.

Figure 1:
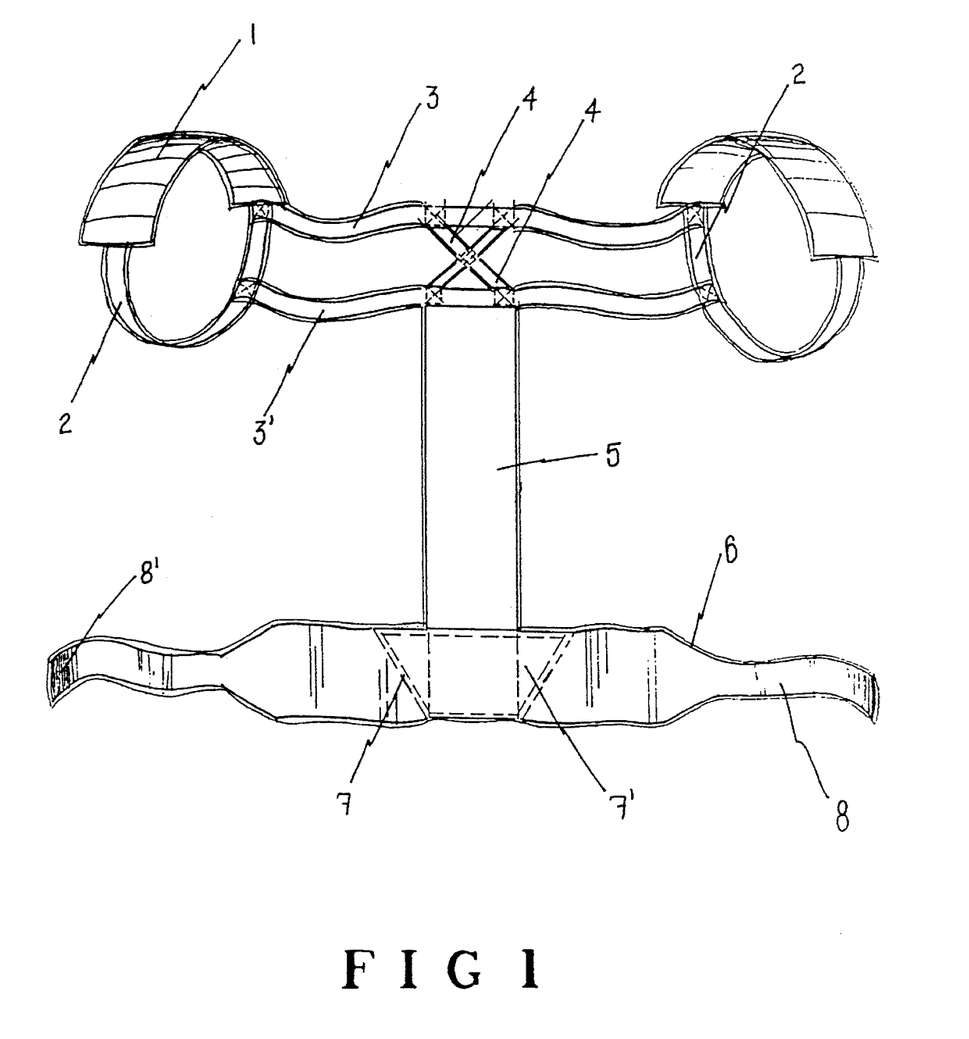
FIG. 1 shows a perspective view of the unfolded harness.
Figure 2:
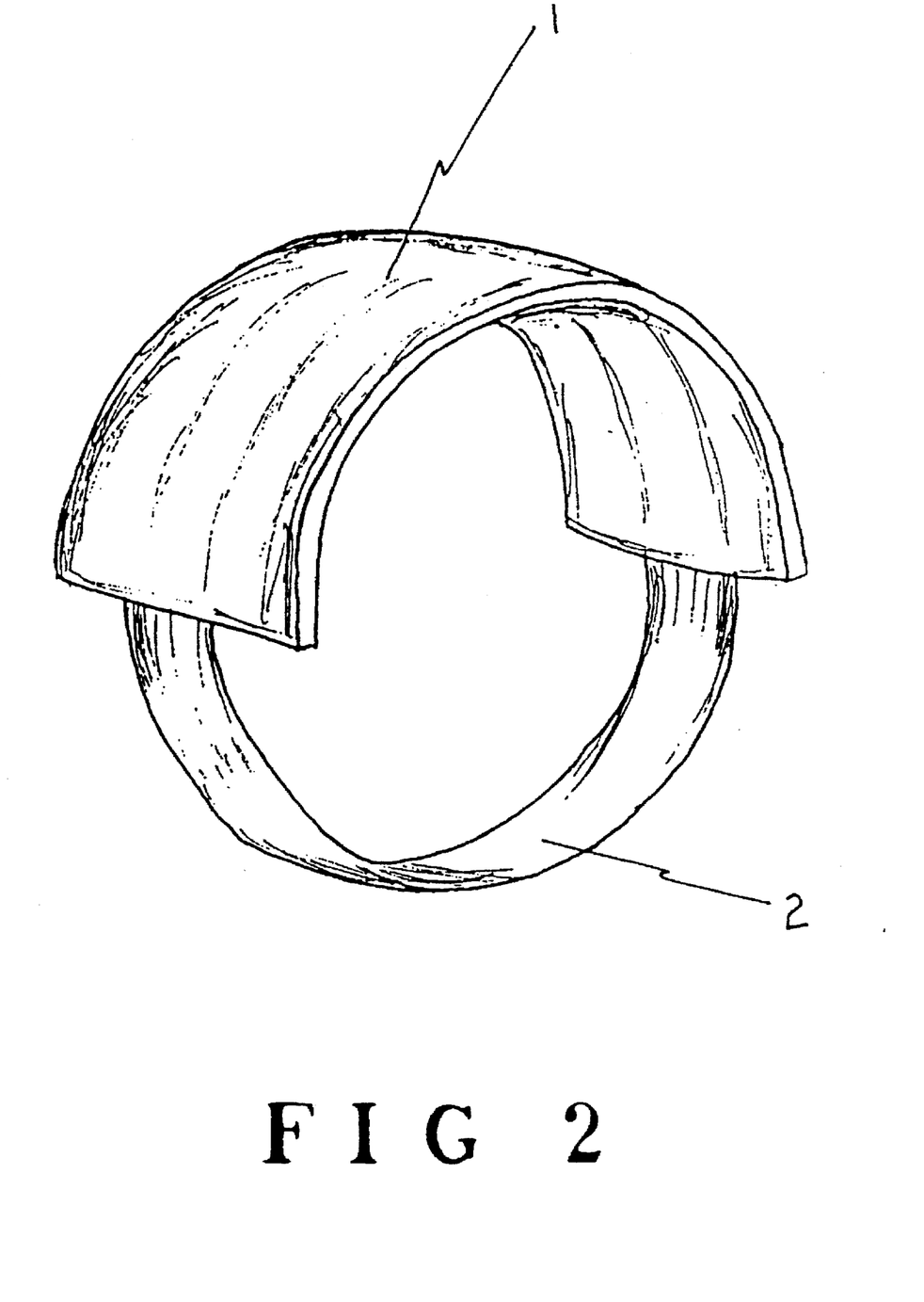
FIG. 2 shows a perspective fragmental view of a scapulothoracic ring.
Figure 3:
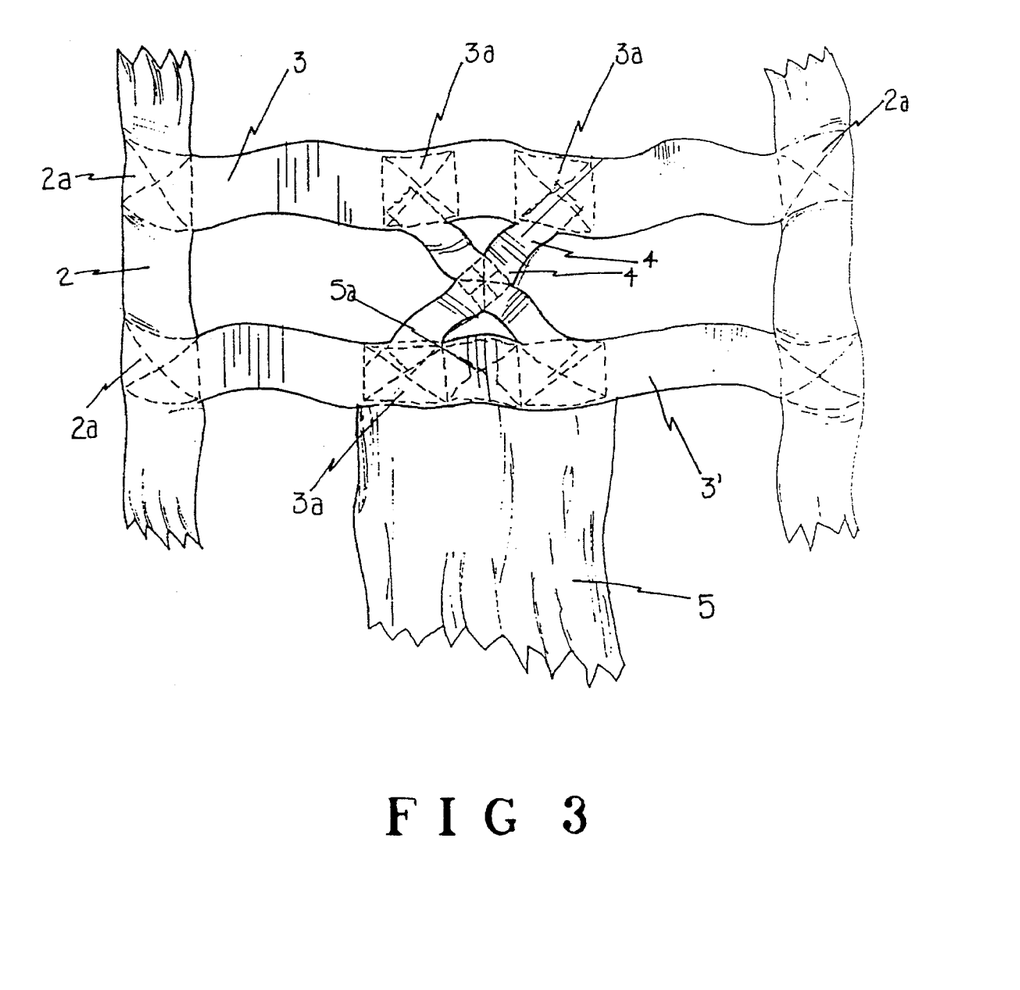
FIG. 3 shows a fragmental front view which illustrates the crossed strap, the upper and lower strap, and part of the scapulothoracic rings.
Figure 4:
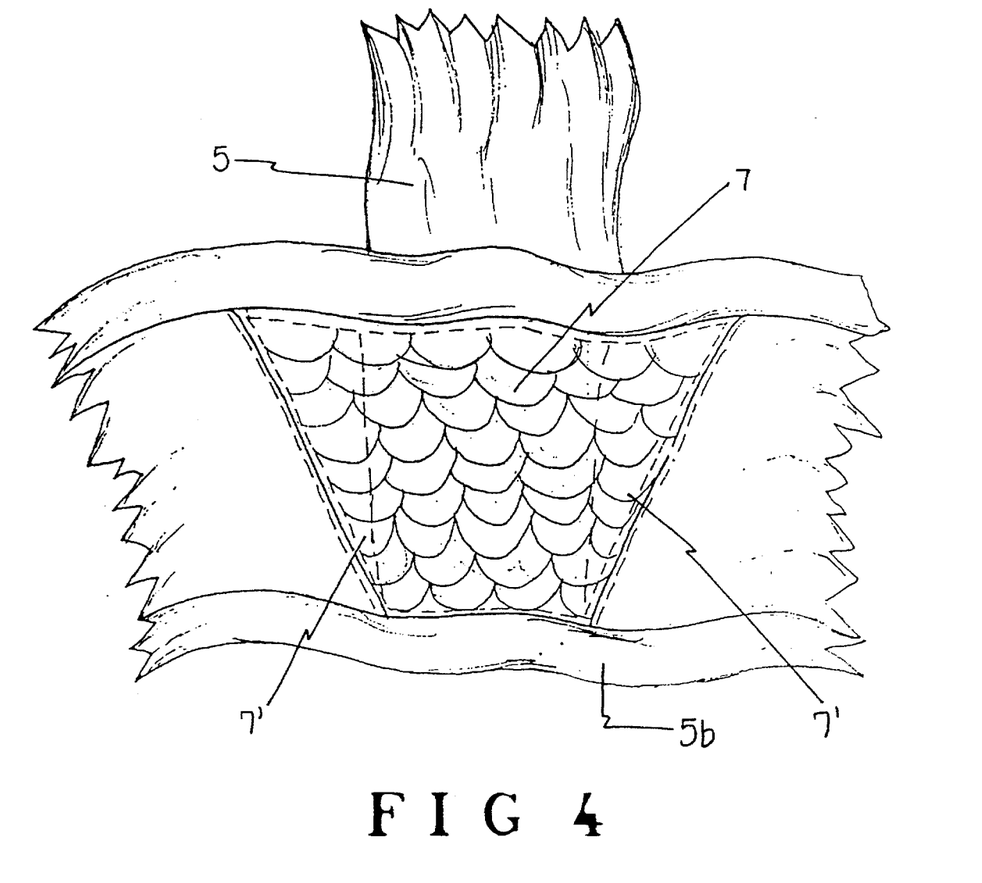
FIG. 4 shows a fragmental front view of the belt with a cushion section.
Figure 5:
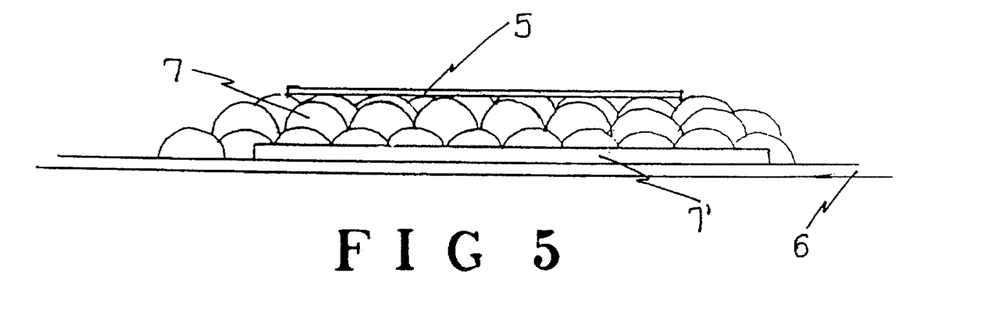
FIG. 5 shows a perspective view of the cushion section.

The dynamic spine harness (FIG. 1) is mainly built with cloth or fabric, its parts joined together by means of seams (2A, 3A, 5A, 5B, FIGS. 3 and 4). The belt part (6) has in its lumbroscral cushion (7) a semiflexible core (7', FIGS. 4 to 6) of plastic or synthetic material. The belt is locked with buckles, "Velcro" or in any other suitable way according to the use it is going to have.

Figure 8:
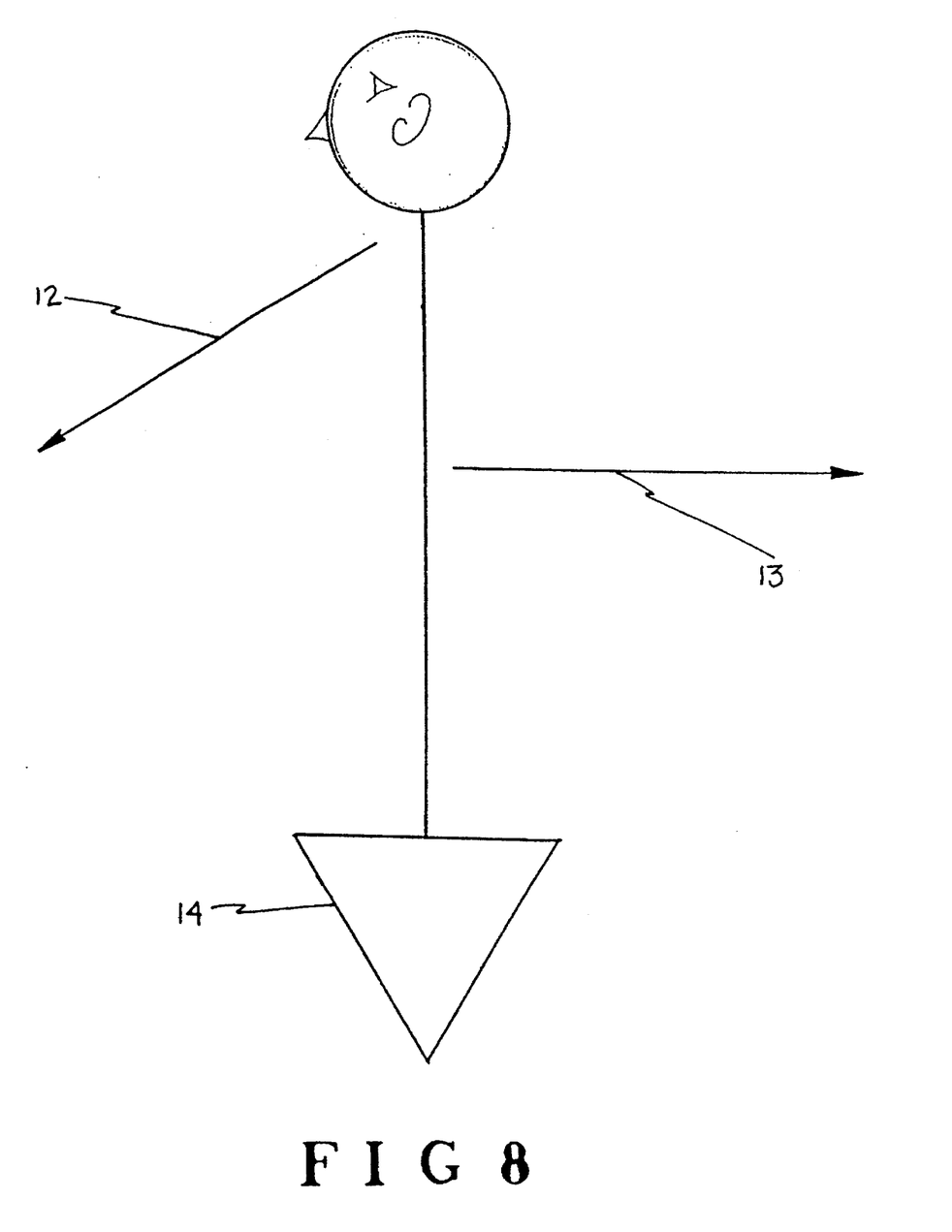
FIG. 8 shows a schematic figure of human body trunk section in erect position.
Figure 9:
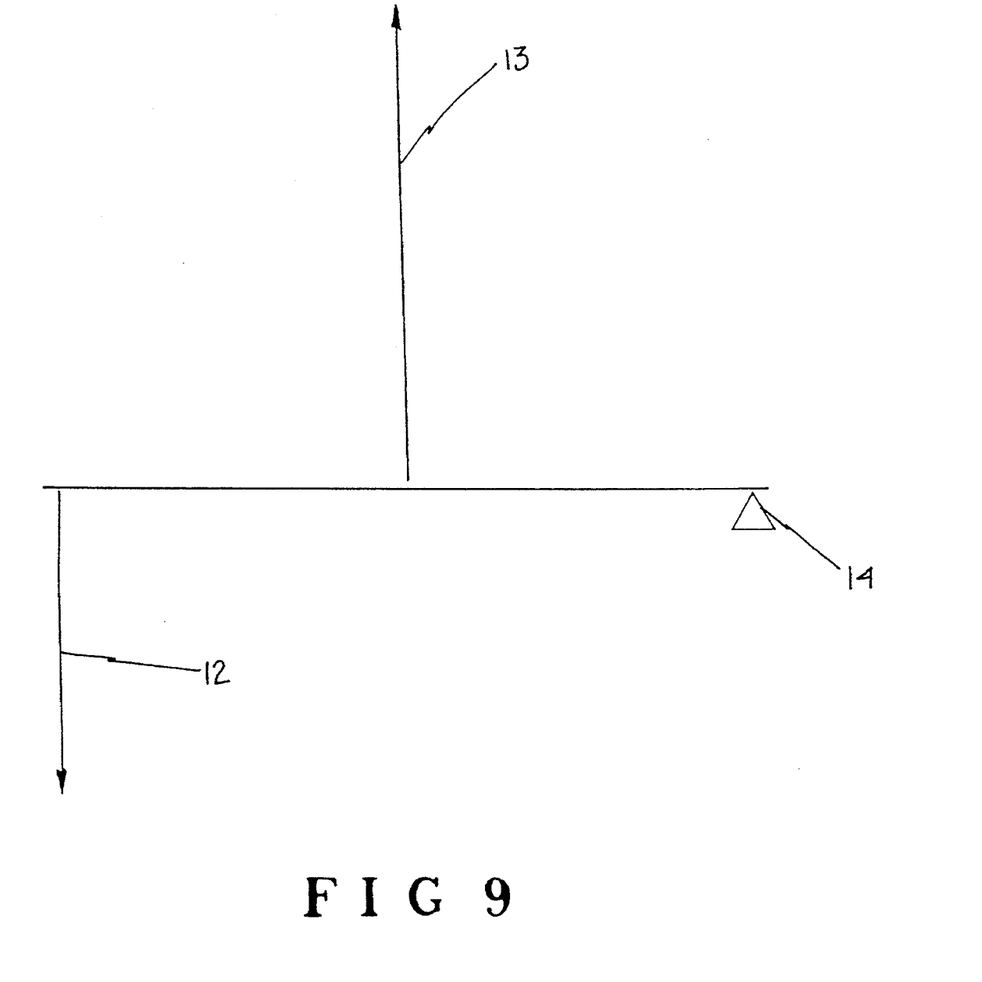
FIG. 9 shows a schematic figure of a simple lever.

Biomechanic considerations of the function of the dynamic spine harness is based on the simple lever principle (FIGS. 8 and 9). A human body, represented by the trunk (FIG. 8), has a body weight resistance force (12), plus the load carried or supported, located in the upper part of the trunk. The body additionally has a support point (14) in the lumbosacral region, and finally a trunk force location (13) representing the force given by tendons, ligaments and specially muscles. The support given by the dynamic spine harness is added to the body support.

In an erect position (FIG. 8) the harness is inactive, as well as in the extension movements of the trunk coming from the erect posture. This provides simplified use and comfort to the user.

During the flexing of the trunk (FIG. 8), beginning at the erect position, the dynamic spine harness becomes active while producing an additional force to the trunk force location (13). In this way an additional mechanical function of the trunk (muscles, ligaments, tendons, muscular fascia) is supplied, thereby avoiding injury because of excessive effort, and limiting damage from repeated flexion-extension movements. In the event of manual loads from objects, the harness helps supplement the muscles. By the harness pressure the user is reminded of the correct position of the spine in doing this job.

In lumbalgia (low-back-pain) cases, caused by injury in the extending mechanism of the trunk (mainly muscle and ligaments), the harness helps these injured structures to function and promotes healing by avoiding additional damage.

What is claimed is:

1. A dynamic orthopedic harness for supporting the human spine in bearing loads and for orthopedic correctional purposes, said harness having a set of interconnected elastically flexible parts for contacting the human body in a support configuration on the shoulders, back and lumbar region of a user, and configured for the user's arms, shoulders, back and waist, comprising in combination:

a pair of scapulothoracic rings for surrounding the user's arms adjacent the shoulders, interconnection means for holding the rings in place, comprising transverse upper and lower elastic straps secured to the rings for resting in a substantially parallel configuration upon the user's back, and crossed suspender straps secured to the upper and lower straps midway to rest upon the user's back, an elastic waistband for disposal about the user's waist to support the lumbar region, and a connection elastic strap respectively secured to the lower transverse elastic strap and the waistband to reside vertically on the back along the spine of the user, said elastic straps and waistband forming a mechanical harness support for fitting on the user to share with the body loads carried by the user and to feedback harness pressures to the user to aid the user in attaining correct posture.

2. The harness of claim 1 further comprising a shaped cushion with a semi-flexible core disposed for contact with the user's back, said cushion being formed in the waistband at a position to cushion and support a lumbosacral region of the user's back.

3. The harness of claim 2 wherein the shaped cushion is generally trapezoidally shaped with a wider upper portion with a contact surface configured for following the normal contour of the user's spine.

* * * * *